(12) United States Patent
Bijno et al.

(10) Patent No.: US 10,300,099 B2
(45) Date of Patent: May 28, 2019

(54) COMPOSITION FOR THE TREATMENT AND PREVENTION OF URINARY TRACT INFECTIONS

(71) Applicant: Kolinpharma S.p.A., Milan (IT)

(72) Inventors: Domenico Bijno, Milan (IT); Carmine Di Vincenzo, Milan (IT); Emanuele Lusenti, Milan (IT); Alberto Martina, Milan (IT); Ritapaola Petrelli, Milan (IT)

(73) Assignee: Kolinpharma S.p.A., Milan (IT)

( * ) Notice: Subject to any disclaimer, the term of this patent is extended or adjusted under 35 U.S.C. 154(b) by 268 days.

(21) Appl. No.: 15/503,083

(22) PCT Filed: Aug. 18, 2015

(86) PCT No.: PCT/IB2015/056270
§ 371 (c)(1),
(2) Date: Feb. 10, 2017

(87) PCT Pub. No.: WO2016/027226
PCT Pub. Date: Feb. 25, 2016

(65) Prior Publication Data
US 2017/0232051 A1   Aug. 17, 2017

(30) Foreign Application Priority Data

Aug. 19, 2014   (IT) .............................. TO2014A0671

(51) Int. Cl.
| | | |
|---|---|---|
| *A61K 36/00* | (2006.01) | |
| *A61K 36/45* | (2006.01) | |
| *A61K 31/05* | (2006.01) | |
| *A61K 31/353* | (2006.01) | |
| *A61K 31/7004* | (2006.01) | |
| *A61K 33/30* | (2006.01) | |
| *A23L 33/105* | (2016.01) | |
| *A23L 33/16* | (2016.01) | |
| *A23L 33/125* | (2016.01) | |
| *A61K 9/00* | (2006.01) | |
| *A61K 31/198* | (2006.01) | |

(52) U.S. Cl.
CPC ............ *A61K 36/45* (2013.01); *A23L 33/105* (2016.08); *A23L 33/125* (2016.08); *A23L 33/16* (2016.08); *A61K 9/009* (2013.01); *A61K 9/0053* (2013.01); *A61K 31/05* (2013.01); *A61K 31/198* (2013.01); *A61K 31/353* (2013.01); *A61K 31/7004* (2013.01); *A61K 33/30* (2013.01); *A23V 2002/00* (2013.01)

(58) Field of Classification Search
CPC ...................................................... A61K 36/00
USPC ........................................................ 424/725
See application file for complete search history.

(56) References Cited

FOREIGN PATENT DOCUMENTS

RU       2021342 C1  *  10/1994

\* cited by examiner

*Primary Examiner* — Michael V Meller
(74) *Attorney, Agent, or Firm* — MacMillan, Sobanski & Todd, LLC

(57) ABSTRACT

A pharmaceutical composition or dietary supplement is described that is effective in the treatment and prevention of urinary tract infections, comprising a combination of D-mannose, proanthocyanidins, hydroquinone derivatives and zinc.

5 Claims, No Drawings

COMPOSITION FOR THE TREATMENT AND PREVENTION OF URINARY TRACT INFECTIONS

This is a national stage application filed under 35 U.S.C. § 371 of international application PCT/IB2015/056270, filed under the authority of the Patent Cooperation Treaty on Aug. 18, 2015, published; which claims the benefit of Patent Application No. TO2014A000671, filed on Aug. 19, 2014. The entire disclosures of all the aforementioned applications are expressly incorporated herein by reference for all purposes.

The invention relates to a composition to be used in the field of the treatment and prevention of urinary tract infections, especially bacterial infections of the urinary tract, such as cystitis, for example.

The subject matter of the invention is a formulation for administration by the oral route, without particular contraindications whether in relation to the subjects to whom it can be administered or in relation to the administered amounts, having an anti-adhesive, diuretic, and antiseptic action and potentiating the immune defences, and therefore effective in the treatment of urinary tract infections.

The composition according to the present invention, effective in the treatment of urinary tract infections, is characterized in that it comprises, as active ingredients, a combination of D-mannose, proanthocyanidins, hydroquinone derivatives and zinc.

Further features of the composition of the invention and of the use thereof are defined in the appended claims, which form an integral part of the present description.

The composition according to the invention is indicated both for prophylaxis, and for reducing acute symptoms. It is designed for obtaining optimum synergy between its components.

The composition according to the invention is designed to neutralize the adhesive capacity of the main uropathogens (including *Escherichia coli*), characterized by the presence of mannose-sensitive and mannose-resistant fimbriae, and to eliminate the situation of bacteriuria that develops, by increasing the urinary flow. An important feature of the composition is the presence of zinc, which is indispensable for restoring the functions of the immune system, which has been compromised by the massive presence of pathogens in the case of infections.

The key component of the product is a dry cranberry extract, preferably the extract marketed as PACRAN®, or the dry cranberry extract obtained using the whole fruit (skin, seeds and pulp). Thus, the product contains not only the A-type proanthocyanidins (present in all the conventional cranberry extracts, with anti-adhesive activity confirmed by numerous studies), but also the entire phytocomplex consisting of organic acids, phenols, fibres, fatty acids and sugars. The cranberry phytocomplex guarantees synergy between the components of which it is constituted, preserving and increasing the total activity of interest. The proanthocyanidins are present in numerous foodstuffs (for example apple, chocolate, grapes), but the A-type proanthocyanidins (characterized by a particular bond between the monomers of which they are constituted) are the only ones that have shown anti-adhesive activity against uropathogens. They have high affinity for the P fimbriae of bacteria (protein structures with which the pathogen binds to the receptors present on the bladder mucosa to initiate the process of infection) to which they bind, saturating them, thus preventing the bacteria infecting the tissue. A fundamental feature of the proanthocyanidins in dry cranberry extract (PACRAN®) is significant polymerization. The proanthocyanidins are not in fact single molecules, but dimers, trimers or polymers of catechins and/or epigallocatechins, bound by means of type A or B bonds. The proanthocyanidins in question are characterized by the presence of more than ten monomers (bound together by type A bonds), slowing metabolization at the intestinal level, ensuring activity of the latter in the site of interest for a prolonged time.

It is known that the bacterial uropathogens are characterized by a wide variety of fimbriae, of varying kinds. The fimbriae present in greatest concentration are the type P fimbriae (mannose-resistant) and the type I fimbriae (mannose-sensitive), which at the level of the bladder recognize the glycosylated receptors, initiating the infective process.

D-mannose is a monosaccharide which, once absorbed in the body, is not accumulated in the liver, but is concentrated in the kidneys and is then transported to the bladder. It arrives there in high concentrations and succeeds in saturating the type I fimbriae, for which it has extremely high affinity, competing with the glycosylated protein fractions. D-mannose thus constitutes the second component of the composition of the invention and operates in synergy with the dry cranberry extract (PACRAN®), complementing its anti-adhesive activity.

*Arctostaphylos uva-ursi* is present in the composition of the invention as a phytocomplex. As in the case of the phytocomplex present in dry cranberry extract, here too the presence of the entire phytocomplex makes it possible largely to preserve the activity and stability of the individual components. In the case of urinary tract infection this proves particularly interesting owing to the presence of molecules with antiseptic activity (arbutin) and molecules with diuretic activity (ursolic acid and tannins).

Arbutin is hydrolysed in the intestine to glucose and hydroquinone; the latter is absorbed and undergoes glucuronidation in the liver. The glucuronidated hydroquinone is transported to the kidneys and is secreted in the urine. At the level of the bladder, numerous studies confirm, in the case of recurrent cystitis, antiseptic activity of the molecule under consideration.

Finally, the composition of the invention comprises an immunomodulating element capable of supporting and potentiating the immune defences, weakened by the presence of pathogens in the case of infections, namely zinc, a fundamental element for numerous biochemical reactions in the body.

It has in fact been demonstrated that in zinc deficiency situations the white blood cells are less efficient. Zinc in fact has an influence on many aspects of the immune system (neutrophils, natural killer cells, phagocytosis, production of cytokines, production of antibodies as well as gene regulation in lymphocytes).

Zinc is moreover involved in many basic cellular functions including DNA replication, RNA transcription, cell division and activation and stabilization of cell membranes. In an especially preferred embodiment, zinc is present in the composition of the invention as zinc bisglycinate chelate.

The combination of the aforementioned active ingredients in the composition according to the invention is particularly advantageous as they develop a synergistic effect.

The compositions of the invention can be formulated in any form suitable for oral administration, for example as hard or soft gelatin capsules, tablets, effervescent or chewable tablets, granules or powders in sachets, solid forms with controlled release, chewing gums and the like.

The compositions of the present invention can be formulated suitably for administration by the oral route and will be prepared by conventional methods well known in pharmaceutical technology, such as those described in "Remington's Pharmaceutical Handbook", Mack Publishing Co., N.Y., USA, using excipients, diluents, fillers, and anti-agglomerating agents acceptable for their end use.

The following experimental section describes the studies that were carried out relating to the biological effects of the composition of the invention.

Moreover, a particularly preferred formulation of the composition of the invention, used in experimental studies, is given below.

FORMULATION EXAMPLE—3-g Sachet

| | |
|---|---|
| D-mannose | 500 mg |
| Cranberry dry extract | 250 mg |
| of which proanthocyanidins | 18 mg |
| Arctostaphylos uva-ursi dry extract | 125 mg |
| of which hydroquinone derivatives | 25 mg |
| Zinc (from zinc bisglycinate) | 6.25 mg |

The recommended dose is one or two daily sachets.

EXPERIMENTAL SECTION

Rationale

Urinary tract infections are among the most commonly encountered infections both in the community and at the nosocomial level. Generally they result from colonization by the ascending route, by microorganisms of enteric origin, for example Escherichia coli. E. coli is in fact considered to be responsible for about 90% of urinary tract infections contracted in the community and for the majority of nosocomial infections. The first step in the pathogenesis of urinary tract infections is represented by adhesion of the pathogen to the uroepithelial cells, which is often mediated by bonds of specific bacterial structures, such as fimbriae.

In recent years it has been demonstrated that administration of cranberry proves effective in reducing the incidence of urinary tract infections, especially those caused by E. coli, in particular preventing recurrent infections. This action seems to be due principally to the interaction of the proanthocyanidins contained in cranberry with the adhesins present on the fimbriae of E. coli. This interaction results in a conformational change of the P fimbriae, which leads to a decrease in the bacterium's capacity for adhesion to the uroepithelial cells.

Purpose of the Study

The present study had a dual purpose:
1. Evaluation of antibacterial activity by determining the minimum inhibitory concentration (MIC) with respect to 10 strains of E. coli isolated clinically, responsible for urinary tract infections.
2. Evaluation of the interference of sub-inhibitory concentrations of the test product on the adhesiveness of E. coli to uroepithelial cells by light microscopy and scanning electron microscopy.

Materials and Methods

Ivuxur

The following experimental tests used the formulation in sachets of the Formulation Example given above, called Ivuxur. For these experiments, Ivuxur was suspended in brain-heart infusion broth (BHI) at a concentration of 100 mg/mL, obtaining partial dissolution of the product.

Bacterial Strains

Ten strains of E. coli isolated in the Laboratory for Chemical, Clinical and Microbiological Analysis of IRCCS Galeazzi from subjects with urinary tract infection without any connection between them were taken into consideration. The strains had a varying profile of antibiotic sensitivity. They were frozen at −80° C. in BHI+10% glycerol until use.

Determination of the Minimum Inhibitory Concentration (MIC)

The MIC of the test product (Ivuxur) was determined by the method of microdilution in broth according to the EUCAST protocol. In particular, the wells of a microtitration plate containing scalar dilutions of Ivuxur were inoculated with a bacterial suspension (bacterial load $10^8$ CFU/mL) in such a way that each well contained $10^5$ CFU of bacteria. For each bacterial strain, one well not containing the compound was used as growth control. After incubation for 16-18 h at 37° C. in an aerobic atmosphere, MIC was determined as the lowest concentration of the compound capable of inhibiting bacterial growth.

Evaluation of the Interference of Sub-Inhibitory Concentrations of Ivuxur on Bacterial Adhesiveness Uroepithelial Cells The uroepithelial cells were obtained from apparently healthy women (aged 22-45 years), who had not received antibiotic treatment for at least 1 month. The cells were washed 3 times with PBS in order to remove any adhering bacteria and were resuspended at a final concentration of $1\times10^5$ cells/mL.

Bacterial Strains

To evaluate the anti-adhesive activity of the compound, two strains of E. coli were used (E. coli 22 and E. coli 36) with different sensitivity to the test compound (Table 1) and a different profile of antibiotic sensitivity, representative of those used in the preceding step of the study. Each strain was incubated for 24 h in BHI broth in the presence of concentrations of Ivuxur equal to ½ and ¼ MIC. At the end of the incubation period, after washing several times with PBS by centrifugation, an inoculum equal to $1\times10^8$ CFU/mL was incubated.

Test of Adhesiveness

The uroepithelial cells collected, as described above, were incubated with the 2 bacterial strains ($1\times10^8$ CFU/mL) grown in the presence or in the absence of Ivuxur at the concentrations stated above. After incubation for 1 hour at 37° C. in an atmosphere containing 5% $CO_2$, the non-adhering bacteria were removed by washing 3 times with PBS, after the last of which the pellet obtained was resuspended in a small amount of PBS. 10 μL of the suspension obtained was deposited on a microscope slide and, after fixing in methanol, was submitted to Gram staining. Another aliquot was deposited on a slide for electron microscopy and, after fixing with glutaraldehyde, it was treated for observation in scanning electron microscopy.

The number of adherent bacteria per cell was determined by counting, in the light microscope, the bacteria adhering to 40 cells, and calculating the average value. The counts of the bacteria adhering to 40 cells were carried out in duplicate by two independent observers. Each experiment was carried out in duplicate.

The index of inhibition of adhesiveness was calculated using the following formula:

I.A. (%)=100−(average number of adherent bacteria per cell after treatment with Ivuxur/average number of untreated bacteria per cell)×100

Results

Antibacterial Activity

The MIC values obtained for the 10 strains of *E. coli* considered are given in Table 1. The concentrations of Ivuxur capable of inhibiting growth of the strains under consideration were found to be between 25 and 100 mg/mL. The concentration capable of inhibiting growth of 50% of the strains (MIC50) was equal to 50 mg/mL while that capable of inhibiting growth of 90% (MIC90) of the strains examined was equal to 100 mg/mL.

Anti-adhesive Activity

For evaluating the anti-adhesive capacity of Ivuxur, two strains of *E. coli* were used, displaying different sensitivity to the test compound: *E. coli* 22 (MIC 25 mg/mL) and *E. coli* 36 (MIC 50 mg/mL).

Table 2 gives the number of adherent bacteria per cell after treatment with sub-inhibitory concentrations of Ivuxur. It can be seen that there is a marked reduction in bacteria capable of adhering to uroepithelial cells after incubation for 12 hours with the test compound, relative to the same bacteria grown in the absence of Ivuxur. The anti-adhesive activity is found to be concentration-dependent, and is more marked for concentrations equal to ½ MIC for both bacteria. The index of inhibition of adhesiveness was equal to 72±8.54% for ½ MIC and 52.8±8.78% for ¼ MIC.

The anti-adhesive activity of Ivuxur was confirmed by examination by scanning electron microscopy. The number of adherent bacteria in one uroepithelial cell was notably reduced after incubation of the bacteria with sub-inhibitory concentrations of the compound being evaluated.

CONCLUSIONS

Ivuxur demonstrated notable anti-adhesive capacity with respect to *E. coli* that are responsible for urinary tract infections.

TABLE 1

Antibacterial activity of Ivuxur with respect to *E. coli*

| Strain | MIC (mg/mL) |
|---|---|
| *E. coli* 22 | 25 |
| *E. coli* 23 | 50 |
| *E. coli* 24 | 50 |
| *E. coli* 25 | 100 |
| *E. coli* 27 | 100 |
| *E. coli* 28 | 50 |
| *E. coli* 33 | 50 |
| *E. coli* 34 | 100 |
| *E. coli* 35 | 50 |
| *E. coli* 36 | 50 |

TABLE 2

Anti-adhesive activity of Ivuxur with respect to *E. coli*

| Strain | Control | ½ MIC | ¼ MIC |
|---|---|---|---|
| | No. of adherent bacteria/cell | | |
| *E. coli* 22 | 25.4 | 8.6 | 13.03 |
| *E. coli* 36 | 41.6 | 8.98 | 17.01 |

The invention claimed is:

1. A tablet or capsule consisting essentially of zinc bisglycinate, cranberry fruit extract and bearberry extract.

2. The tablet or capsule of claim 1, wherein the cranberry fruit extract has a proanthocyanidins titre of 7.2%.

3. The tablet or capsule of claim 1, wherein the bearberry extract is a leaf extract and has a hydroquinone derivatives titre of 20%.

4. The tablet or capsule of claim 1, consisting essentially of from 450 to 550 mg of D-mannose, from 200 to 300 mg of the cranberry fruit extract, from 100 to 150 mg of the bearberry extract, and from 5 to 10 mg of zinc bisglycinate.

5. The tablet or capsule of claim 1 which can be used to treat a urinary tract infection.

\* \* \* \* \*